(12) United States Patent
O'Beirne et al.

(10) Patent No.: US 7,101,719 B2
(45) Date of Patent: *Sep. 5, 2006

(54) SUPPORT AND METHOD FOR CELL BASED ASSAYS

(75) Inventors: Gerard Bernard O'Beirne, Amersham (GB); Rahman Aziz Ismail, Amersham (GB); Nicholas Thomas, Amersham (GB)

(73) Assignee: GE Healthcare Limited, Amersham (GB)

( * ) Notice: Subject to any disclaimer, the term of this patent is extended or adjusted under 35 U.S.C. 154(b) by 401 days.

This patent is subject to a terminal disclaimer.

(21) Appl. No.: 09/992,111

(22) Filed: Nov. 5, 2001

(65) Prior Publication Data

US 2002/0094543 A1 Jul. 18, 2002

(30) Foreign Application Priority Data

Nov. 10, 2000 (GB) .................................. 0027516.4

(51) Int. Cl.
G01N 33/534 (2006.01)
C12N 5/00 (2006.01)
B32B 5/02 (2006.01)
G01N 33/557 (2006.01)

(52) U.S. Cl. .............................. 436/545; 435/2; 435/3; 435/7.2; 435/29; 435/35; 435/7.92; 435/374; 435/403; 436/56; 436/57; 436/63; 436/164; 436/517; 436/524; 436/528; 422/71

(58) Field of Classification Search .................... 435/4, 435/7.1, 7.2, 29, 35, 7.92, 1, 1.2, 2, 3, 5, 435/30, 39, 373, 374, 385, 395, 403, 284.1, 435/287.2, 288.4; 436/57, 63, 531, 535, 436/537, 804, 805, 18, 56, 164, 165, 517, 436/524, 528; 422/71, 68.1; 250/485.1, 250/486.1, 487.1

See application file for complete search history.

(56) References Cited

U.S. PATENT DOCUMENTS 5,512,474 A * 4/1996 Clapper et al. ............. 435/402
5,989,854 A * 11/1999 Cook .......................... 435/35
6,524,786 B1 * 2/2003 Jessop .......................... 435/4

FOREIGN PATENT DOCUMENTS

WO WO 96/19739 * 6/1996

OTHER PUBLICATIONS

Cook, N.D., Scintillation Proximity Assay: a versatile high-throughput screening technology, Drug Discovery Today, vol. 1 (7): 287-294 (1996)).*

* cited by examiner

*Primary Examiner*—Long V. Le
*Assistant Examiner*—Gailene R. Gabel
(74) *Attorney, Agent, or Firm*—Yonggang Ji

(57) ABSTRACT

Disclosed is a method for the measurement of a cellular process, or for the measurement of the effect of a test compound on a cellular process, in one or more different populations of cells. The method comprises providing separate samples of one or more different populations of cells adhering to support particles, the support particles comprising a scintillant substance and being adapted for cell growth. In one embodiment, different samples of cells are introduced into separate reaction vessels in a fluid medium, together with a reagent labelled with a radioisotope, in the presence or the absence of the test compound, under conditions so as to cause a portion of said radiolabelled reagent to become associated with the cells. In another embodiment, multiparameter analysis may be performed to determine the effect of a test compound on a cellular process using two or more different cell populations present in the same well. Measurement of the cellular process, or the effect of a test compound on a cellular process may be made by detecting light emission from the scintillant particles caused by radioactive decay of the radioisotope.

10 Claims, 4 Drawing Sheets

Uptake of [35S]Methionine into CHO cells grown on CYTODEX™ Microcarrier Beads containing Yttrium Oxide (YOx) +/- Cycloheximide

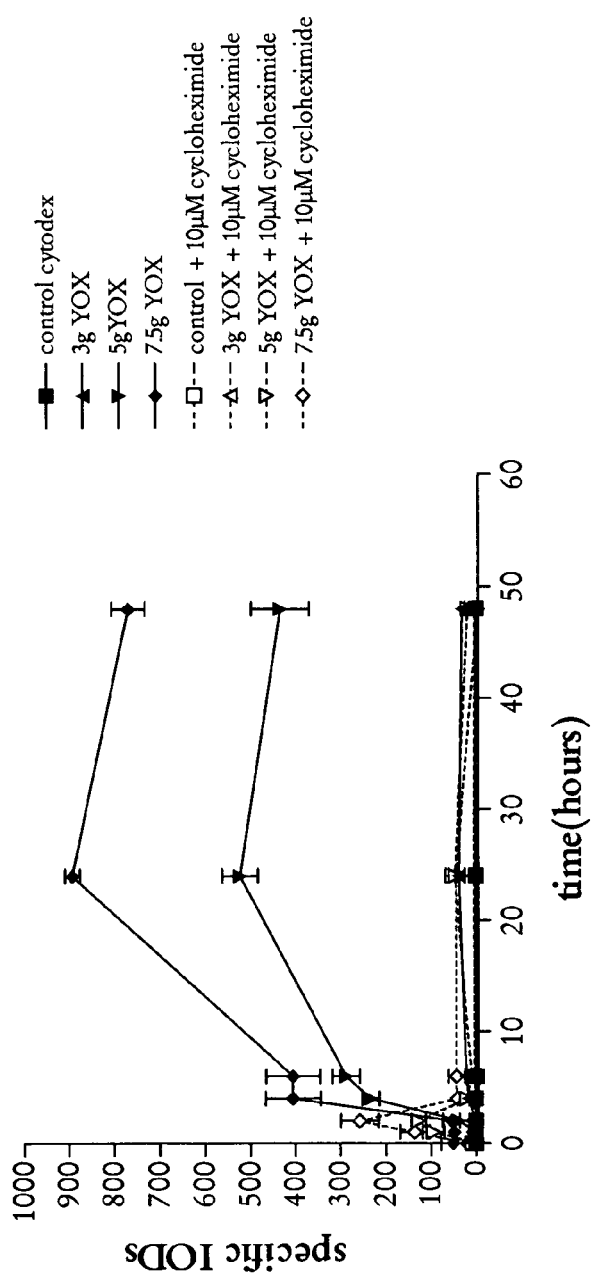
Figure 1: Uptake of [³⁵S]Methionine into CHO cells grown on CYTODEX™ Microcarrier Beads containing Yttrium Oxide (YOx) +/- Cycloheximide

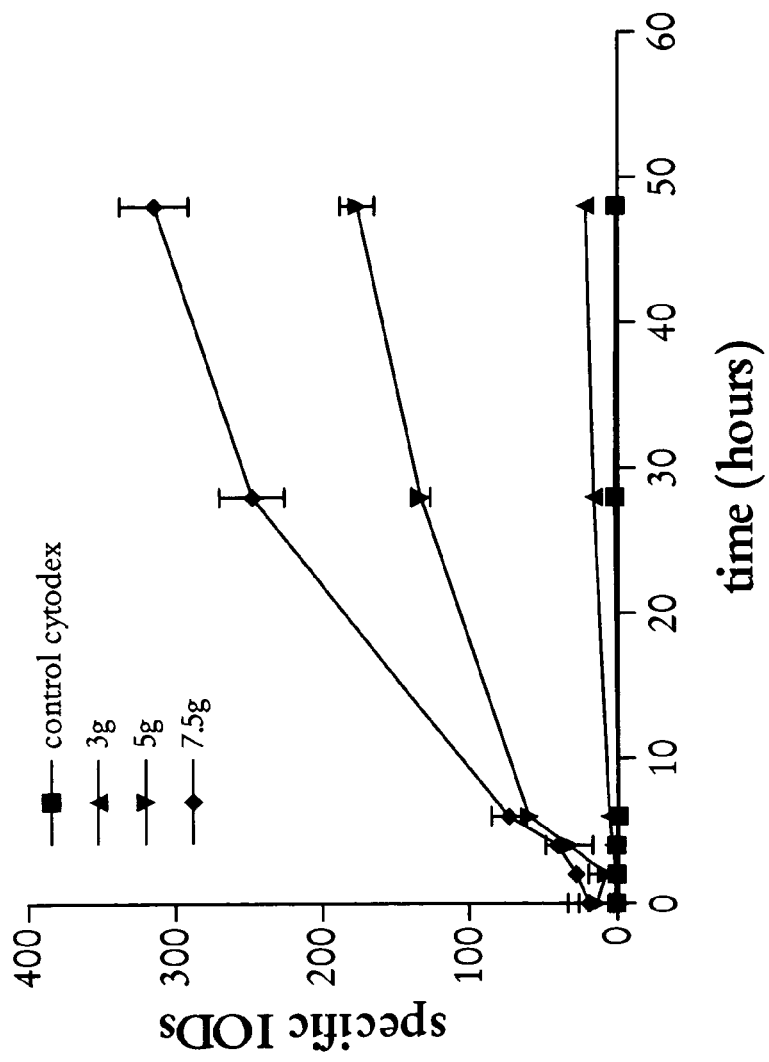
Figure 2: Uptake of [14C]Methionine into CHO cells grown on CYTODEX™ Microcarriers containing Yttrium Oxide (YOx)

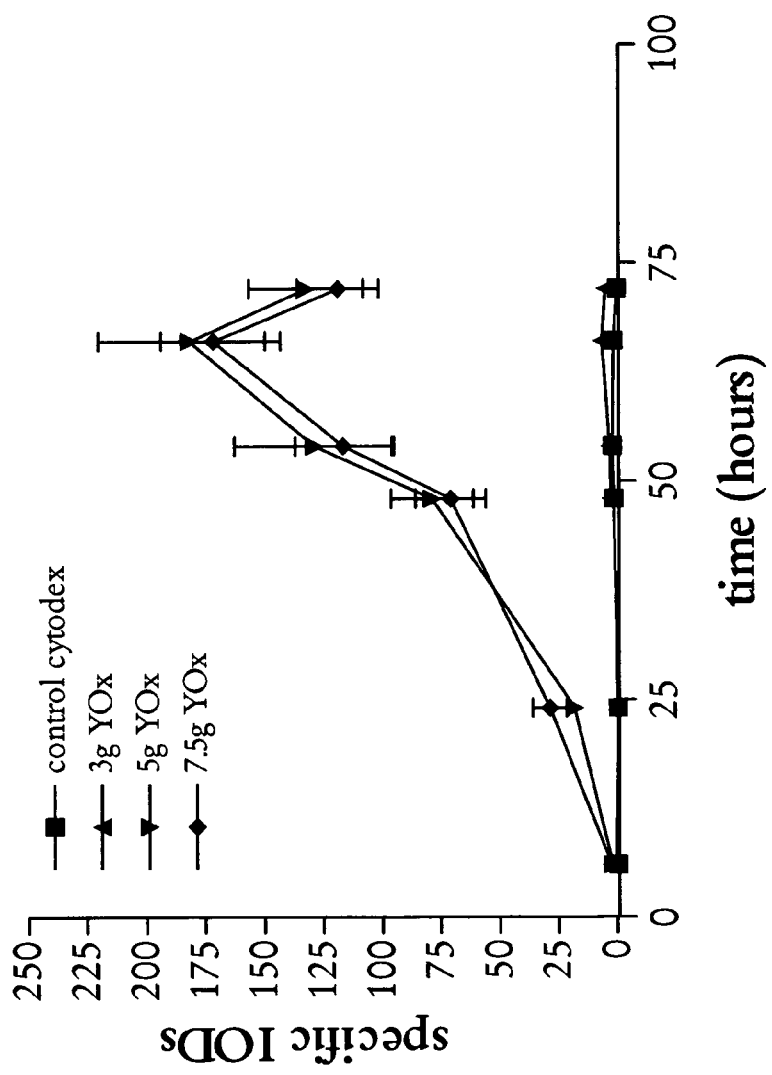
Figure 3: Uptake of [3H] Methionine into CHO cells grown on CYTODEX™ Microcarriers containing Yttrium Oxide (YOx)

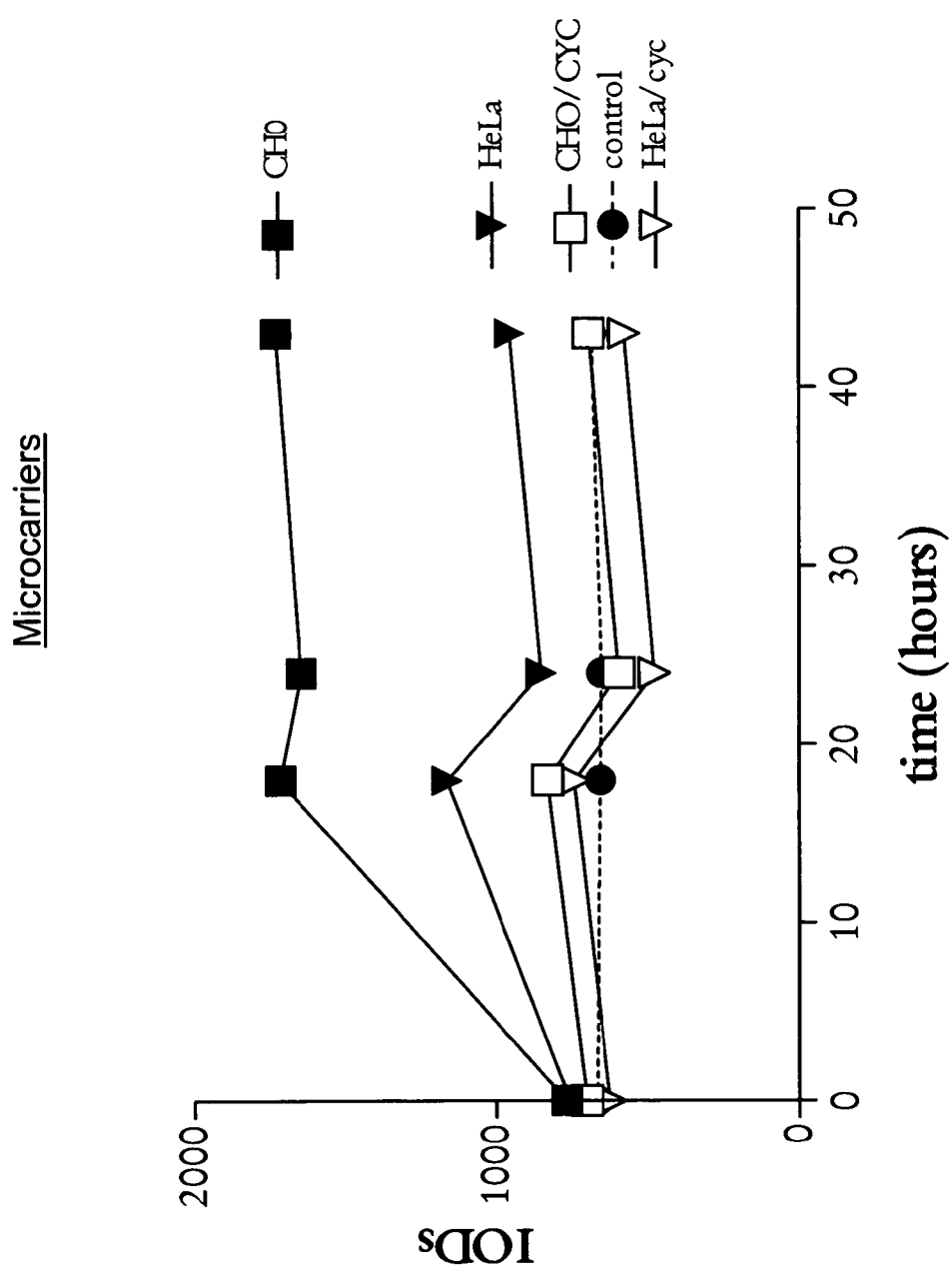
Figure 4: Incorporation of [35S]methionine into CHO and HeLa cells growing on CYTODEX™-YOX Microcarriers

SUPPORT AND METHOD FOR CELL BASED ASSAYS

The present invention relates to cell based assays used in pharmaceutical drug screening and toxicological testing applications. In particular, the invention relates to a method for determining the effects of external agents on one or multiple cell types, in parallel assays. The assays of the invention utilise scintillant-containing support particles (microcarriers) that are adapted for cell growth.

BACKGROUND OF THE INVENTION

The application of high-throughput screening (HTS) technologies for the discovery and development of new therapeutic drugs is now well established within the pharmaceutical industry. In the HTS process, drug candidates are screened for possible effects in biological systems and for the specificity of selected lead compounds towards particular targets. Primary screening has been addressed by the development of HTS assay processes and assay miniaturisation utilising the microtitier well plate format with 384, 864, 1536 or greater miniaturised wells and are capable of allowing throughput levels of over 100,000 tests/day in primary screening. Lead compounds identified during the primary screening process are then required to undergo further refined screening and testing in a variety of assays in order to investigate the biological compatibility of the compound. Such assays may include receptor binding and enzyme activity assays, in addition to bioavailability, metabolism and toxicology. Secondary screening of lead compounds can identify potentially undesirable side effects and/or secondary therapeutic activities not identified in the primary screening process and these assays are carried out predominantly using cultured cell lines. In comparison with assays used in the primary screening process, secondary screening assays have a much higher level of complexity and more stringent requirements, both in the mechanics of the assay and in the information generated.

The detection of in vitro binding events, such as receptor binding assays, enzyme assays and immunoassays using scintillation proximity assays (SPA) is now an established technology and is used in HTS applications (Cook, N. D., Drug Discovery Today, Vol 1 (7), (1996), 287–294). SPA utilises scintillant-containing microspheres to which ligands (eg. antibodies, binding proteins, etc) have been attached. When a radioisotopically labelled molecule is brought into close proximity to the scintillant in the microsphere, energy transfer from the radioisotopic decay takes place, resulting in the emission of light. Any radioisotope remaining free in solution, will dissipate its energy into the aqueous medium and will remain undetected. SPA has also been applied to the study of cellular biochemical processes in situ, using cultured living cells. European Patent No. 650396 discloses a method and an apparatus for studying a cellular process, for example, a microwell plate. Each well of the microwell plate includes a scintillant layer in the base, which is further treated to facilitate the attachment and/or growth of cells. In an alternative format, the device may be a single well or tube which is composed of a non-scintillant containing material, into which is placed a circular, scintillant-containing plastic disc. The method for studying a cellular process includes culturing cells adhering to the scintillant layer, in the presence of a fluid medium, introducing into the fluid medium a reagent labelled with a radioisotope emitting electrons, such that a portion of the labelled reagent becomes associated with or released from the cells adhering to the layer. Scintillation events caused by the proximity of the radiolabelled reagent to the scintillant containing base are detected so as to study the cellular process.

PCT Application No. WO97/40189 relates to a method for quantifying the amount of target nucleic acid such as mRNA in morphologically intact cells, the method comprising the steps of culturing not less than two physically distinct samples of cells on at least one substrate, contacting the cells with a fixative and exposing the fixed cells to a labelled nucleic acid probe to hybridise with the target nucleic acid sequence. This invention is concerned therefore with measurements of hybridisation of nucleic acid probes to fixed cells following processing and washing. The method of the invention does not describe and is not compatible with measurement of dynamic processes in living cells.

PCT Application No. WO 96/19739 describes a solid support for use in radioligand binding assays, the support comprising a plurality of interconnected elements arranged to provide interstitial spaces in which a liquid can flow. The support comprises plastic beads which, in a preferred form may contain a scintillant, and which are fused together to form a solid support for in vitro binding assays. While the solid support may also be used for cell growth, it is stated that the support should preferably not contain a fluorophore.

The use in cell culture of CYTODEX™ Microcarrier support particles (Amersham Pharmacia Biotech) has improved the yields of anchorage dependant cells by increasing the surface area for growth. Properties of these microcarriers include optimised size and density for maximum cell growth, a biologically inert matrix that provides a strong but non-rigid substrate for stirred cultures and transparency for easy microscopic examination of attached cells. Microcarriers can be used in either suspension cultures or monolayer cultures to increase the surface area of the culture vessels and perfusion chambers. The increased surface area allows enables the production of increased densities of cells, viruses and cell products.

SUMMARY OF THE INVENTION

There is now a requirement in the art for secondary screening assay methodologies which are capable of handling the increasing rate of lead drug generation and which are compatible with free-format cellular assays and, in particular, methodologies which enable several different types of cell types and/or treatments with test agents to be monitored in parallel.

According to a first aspect of the invention there is provided a method for the measurement of a cellular process in one or more different populations of cells, the method comprising:

i) providing one or more different populations of cells adhering to support particles said support particles comprising a scintillant substance and being adapted for cell growth;

ii) introducing samples of said populations of cells in a fluid medium into separate reaction vessels for each population sampled;

iii) introducing into each reaction vessel a reagent labelled with a radioisotope under conditions so as to cause a portion of said radiolabelled reagent to become associated with said cells; and iv) detecting light emission from the scintillant particles caused by radioactive decay of the radioisotope as a means of measuring said cellular process.

According to a second aspect of the invention there is provided a method for the measurement of the effect of a test compound on a cellular process in one or more different populations of cells, the method comprising:

i) providing one or more different populations of cells adhering to support particles said support particles comprising a scintillant substance and being adapted for cell growth;
ii) introducing samples of said populations of cells in a fluid medium into separate reaction vessels for each population sampled;
iii) introducing into each reaction vessel a sample of a test compound whose effect on said cellular process is to be measured;
iv) introducing into each reaction vessel a reagent labelled with a radioisotope under conditions so as to cause a portion of said radiolabelled reagent to become associated with said cells; and
v) detecting light emission from the scintillant particles caused by radioactive decay of the radioisotope as a means of measuring the effect of the test compound on said cellular process.

BRIEF DESCRIPTION OF THE FIGURES

FIG. 1 is a plot showing uptake of [$^{35}$S]methionine into CHO cells grown on CYTODEX™/YOx Microcarrier beads in the presence and absence of the uptake inhibitor cycloheximide according to Example 2.

FIG. 2 is a plot showing uptake of [$^{14}$C]methionine into CHO cells grown on CYTODEX™/YOx Microcarrier beads according to Example 2.

FIG. 3 is a plot showing uptake of [$^{3}$H]methionine into CHO cells grown on CYTODEX™/YOx Microcarrier beads in the presence and absence of cycloheximide according to Example 2.

FIG. 4 is a plot showing the incorporation of [$^{35}$S] methionine into CHO cells and HeLa cells grown on CYTODEX™/YOx Microcarriers in the presence and absence of cycloheximide according to Example 3.

DETAILED DESCRIPTION OF THE INVENTION

In a particular embodiment of the second aspect, the measurement of step v) is compared with a measurement of a cellular process in one or more different populations of cells in the absence of the test compound.

By cellular process, it is meant the normal processes which living cells undergo and includes: biosynthesis, uptake, transport, receptor binding, metabolism, fusion, biochemical response, growth and death. In addition to cellular processes resulting from internalisation of the test compound, the method of the invention may be used to measure events at the cell surface, such as ligand binding to cell surface receptors. In this case, the receptor binding comprises a specific binding interaction between the radiolabelled reagent and a specific binding partner located in or on the surface of the cells. The measurement of the cellular process may be performed in real time using a non-invasive technique.

According to the method of the present invention, one or more different populations of cells are grown separately in cell culture on support particles comprising a scintillant substance. Samples of the different cell populations are arrayed into the wells of a multiwell plate and treated with a radiolabelled reagent and optionally a sample of a test compound whose effect on the cellular process is to be measured. For example, a ligand-receptor interaction or ion uptake by cells, may be studied by treatment of each of the cell samples with different concentrations of the radiolabelled reagent. Alternatively, if the effect of a test compound is to be determined, each of the cell samples may be treated with different concentrations of the test compound in the presence of a fixed quantity of the radiolabelled reagent.

Suitably, one or more different cell types may be used in the method of the invention. Culture of cells on a support according to the present invention involves the use of standard cell culture techniques, eg. cells are cultured in a sterile environment at 37° C. in an incubator containing a humidified 95% air/5% $CO_2$ atmosphere. Alternatively, cells may be cultured in sealed vessels containing an atmosphere of air/5% $CO_2$. Vessels may contain stirred or stationary cultures. Various cell culture media may be used including media containing undefined biological fluids such as foetal calf serum, as well as media which is fully defined, such as 293 SFM II serum free media (Life Technologies Ltd., Paisley, UK). The invention may be used with any adherent cell type that can be cultured on standard tissue culture plastic-ware. Such cell types include all normal and transformed cells derived from any recognised source with respect to species (eg. human, rodent, simian), tissue source (eg. brain, liver, lung, heart, kidney skin, muscle) and cell type (eg. epithelial, endothelial). In addition, cells which have been transfected with recombinant genes may also be cultured and utilised in the method of the invention. There are established protocols available for the culture of diverse cell types. (See for example, Freshney, R. I., Culture of Animal Cells: A Manual of Basic Technique, $2^{nd}$ Edition, Alan R. Liss Inc. 1987). Such protocols may require the use of specialised coatings and selective media to enable cell growth and the expression of specialist cellular functions. None of such protocols is precluded from use with the scintillant-containing support particles used in the method of the invention. Optionally, the cells may be additionally treated with a stain that permits visualisation of the cells cultured on the surface of the support particles. Suitable stains may be selected from crystal violet, neutral red, calcein-AM, Giemsa, Haematoxylin, or other histological stains.

Detection of the light emission from the scintillant containing support particles may be performed by non-imaging counting (such as liquid scintillation counters, or luminometers). Alternatively, detection may be accomplished by imaging techniques, preferably by means of a charge coupled device (CCD) imager (such as a scanning imager or an area imager) to image all of the wells of a multiwell plate. Imaging is quantitative and fast, and instrumentation suitable for imaging applications can now simultaneously image the whole of a multiwell plate.

The effect on cellular structure and function of many types of biomolecules may be studied using the method of the invention. Thus, any molecule that can be radiolabelled and can be transported into, or metabolised by cells, or can interact with the cell surface or bind with cell surface receptors, may in principle be studied. Examples of biomolecules include: amino acids, nucleosides, nucleotides and analogues thereof, oligonucleotides, nucleic acids (eg. DNA and RNA), lipids, hormones, peptides, proteins, carbohydrates, ions (eg. calcium, potassium, sodium, chloride) and receptor ligands. The method is particularly suitable for determining the effect on a cellular process of test compounds, such as those compounds whose metabolism and toxicology towards particular cell types is under investigation. Examples include: drugs, enzyme inhibitors, antagonists and the like.

The method according to the second aspect of the invention is particularly suitable for the parallel analysis of the effect of a test compound on several different cell types and/or treatments, where growth of the different cell types is incompatible in a single multiwell plate. Cells are grown separately on support particles and samples of the different cell populations are arrayed into individual wells of a conventional multiwell plate for treatment with a test compound. The effect of the test compound on the cell process is then determined. The method is particularly suitable for the measurement of the effect of a test substance on cells in real time and where the assay format does not affect the viability or integrity of cells under study.

As an alternative, multiparameter analysis may be performed to determine the effect of a test compound on a cellular process using two or more different cell populations present in the same well. In this embodiment, use is made of different types of support particles, each particle type having a different scintillant substance bound to, or integrated into, the matrix of the particle, wherein each scintillant is capable of emitting spectrally distinct light that may be resolved by imaging. Each different cell type is cultured separately in bulk using a different support particle, and then support particles are combined in a suitable reaction vessel, such as a well of a multiwell plate, prior to the addition of a radiolabelled reagent and a sample of a test compound. Detection of the emissions from the different particle (and hence cell) types is accomplished by CCD-based imaging techniques. Preferably, the measurement of the effect of a test compound may be made on up to three different cell types present in the same well. Particularly preferred are measurements utilising two different cell types.

Suitably, the reaction vessels form the wells of a multiwell plate having 96, 384, 864 wells or more.

Suitably, the radioisotope is one that emits β-particles or electrons having a mean free path of up to 2000 μm in aqueous media. Suitable radioisotopes are those commonly used for labelling biomolecules and used in biochemical applications and include $^{14}C$, $^{3}H$, $^{35}S$, $^{33}P$, $^{125}I$, $^{32}P$, $^{45}Ca$, $^{55}Fe$, $^{51}Cr$, $^{86}Rb$ and $^{109}Cd$.

The present invention also pertains to a support for cell based assays performed according to the method. Thus, in a third aspect there is provided a support for cell based assays, said support comprising particles comprising a matrix and having a scintillant substance which has been coated onto, or integrated into, the matrix of the particles and being adapted for cell growth.

Suitably, the support particles employed in the present invention can be composed of any material compatible with the growth of adherent cells, the support particles containing a scintillant substance which has been coated onto, or integrated into, the matrix of the particles. In a preferred embodiment, the support particles comprise polymeric beads, preferably having a porous or macro-porous structure. Suitable polymeric materials include polystyrene, polyvinyltoluene, polyacrylamide, agarose, polycarbonate or dextran polymers. Particularly preferred supports for use in the method are CYTODEX™ Microcarrier supports which are sold under the Trade Mark, CYTODEX (Amersham Pharmacia Biotech) and consist of a biologically inert cross-linked dextran matrix.

The scintillant substance is preferably coated onto or integrated into the matrix of the support particle, such that when a radiolabelled reagent is brought into close enough proximity with the surface of the particle, the scintillant is caused to emit light. Various types of scintillant substances may be used, and are generally selected from organic scintillators and inorganic scintillators. For example, the scintillant can include aromatic hydrocarbons, such as p-terphenyl, p-quaterphenyl and derivatives, and derivatives of the oxazoles and oxadiazoles, such as 2,5-diphenyloxazole and 2-(4-t-butylphenyl)-5-(4-biphenylyl)-1,3,4-oxadiazole. A wavelength shifter may also be included in the polymeric composition, the function of the wavelength shifter being to absorb light emitted by the primary scintillant material and re-emit light at a longer wavelength which is compatible with photosensitive detectors in scintillation counters. Alternatively, the scintillant may be composed of an inorganic scintillant such as yttrium silicate (YSi) or yttrium oxide (YOx).

The support particle may alternatively include a scintillant substance which is suitable for imaging applications, such as are disclosed in PCT Application No. WO 99/09415. The scintillant substance preferably has an emission maximum in the range 500 nm to 900 nm and consists generally of an inorganic host material doped with an activator. Examples of host materials are yttrium silicate, yttrium oxide, yttrium oxysulphide, yttrium aluminium gallium oxide (YAG), yttrium aluminium garnet, sodium yttrium fluoride ($NaYF_4$), lanthanum fluoride, lanthanum oxysulphide, yttrium fluoride ($YF_3$), yttrium gallate, gadolinium fluoride ($GdF_3$), barium yttrium fluoride ($BaYF_5$ or $BaY_2F_8$), gadolinium oxysulphide, zinc silicate, zinc sulphide and yttrium vanadate. The activator is generally a lanthanide or actinide moiety, and is preferably selected from terbium, europium, erbium, thulium, holmium, dysprosium, samarium, ytterbium, lutecium, gadolinium, uranium and uranyl $UO_2$, generally in the form of +2 or +3 ions. Other suitable scintillators are organic chelates of lanthanide or actinide transition metals, such as an imido phosphorane, as disclosed in EP 556005. In multiparameter analysis applications according to the present invention, different support particles are employed, each particle type having a different scintillant substance bound to, or integrated into, the matrix of the particle. In such applications, scintillant substances suitable for bead (and therefore cell) identification are those which have distinguishably different emission spectra. Suitable scintillators include those having emission in the blue region of the spectrum (for example, PVT and YSi:Ce), in the green region of the spectrum (for example, $Y_3(Al,Ga)_5O_{12}:Tb^{3+}$) and in the red region of the spectrum (for example, $Y_2O_3$:$Eu^{3+}$).

The support particles employed in the present invention must be treated or surface modified to allow cell adherence and cell growth. Various types of support surface treatment may be used, including both physical and chemical treatments. A preferred method for treatment of plastic beads involves the use of high voltage plasma discharge (either vacuum discharge or atmospheric discharge) which is a well-established method for creating a negatively charged hydrophilic surface that allows cell spreading and adherence. Cell adherence and growth can be further enhanced by applying additional coatings to the support surface, including: (i) positively or negatively charged chemical coatings such as polylysine, or other biopolymers, (ii) components of the extracellular matrix, including collagen, laminin, fibronectin, and (iii) naturally secreted extracellular matrix laid down by cells cultured on the plastic surface. In the preferred supports for use in the invention, different types of coated and derivatised CYTODEX™ Microcarrier supports are available, such as that formed by substituting the dextran matrix with DEAE (N,N-diethylaminoethyl) groups distributed throughout the matrix, or by substituting the matrix with a surface layer of positively-charged THAMP (N,N,N- trimethyl-2-hydroxyaminopropyl) groups (CYTODEX™ Microcarriers, Technical Data File; Microcarrier Cell Culture, Principles and Methods, Amersham Pharmacia Biotech).

For integrating scintillant material (such as yttrium oxide or yttrium silicate) into the matrix of CYTODEX ™ Microcarrier support particles, the method typically includes forming an emulsion of a mixture of dextran and the yttrium compound in an aqueous solution, followed by cross-linking.

Preferred support particles for use in the present invention are those in the form of a bead having a diameter in the range from 1 µm to 500 µm, and more preferably in the range from 50 µm to 250 µm.

A principal advantage of using the support particles according to the present invention is the achievement of increased surface area for cell growth compared with conventional cell based assays using cells grown in multiwell plates, which may limit some applications in higher density formats. Miniaturisation of assay formats, for example in 1536 and greater multiwell plates, reduces the surface area available for cell growth and hence reduces the number of cells that may be used in an individual assay measurement. In some applications, a reduction in the number of cells/assay may adversely affect the accuracy and precision of the assay. To overcome this, the method of the invention may be used to increase the numbers of cells in an assay while maintaining the miniaturised format as described in the following example.

For a 2 mm×2 mm square well, typical of a high-density multiwell plate, the surface area of the well base is 4 mm$^2$ or $4 \times 10^6$ µm$^2$. A typical mammalian cell in culture occupies an area of ~200 µm$^2$, hence it is possible to culture ~20,000 cells/well by growing cells directly on the well base. For spherical particles of the invention having a diameter of 175 µm, particle area ($4\pi r^2$) is ~385,000 µm$^2$ which will support the growth of ~1925 cells/particle. If these particles are arrayed in the base of the same 2 mm×2 mm well described above the well can contain ~130 particles (assuming the beads are packed as a two-dimensional array), this number of beads supports the growth of ~250,000 cells (~130 particles×~1925 cells/particle), an increase in cell numbers of 12 fold over growth of cells directly on the base of the well. Further increases in cell numbers may be achieved if required, by the addition of more beads such that multiple layers of beads are formed in the well.

A further advantage of the method of the invention for improving accuracy and precision in miniaturised assays is provided by the ability to use the particles of the invention to grow cells in bulk culture, for example in large stirred cultures, and subsequently to subdivide the bulk culture by dispensing fractions of the culture into individual wells of microwell plates for assay. Growth in, and dispensing from, a bulk culture provides a means of delivering a tightly controlled number of cells to each assay well, and avoids the variance in cell number which may occur for cell cultures grown for extended periods of time in miniaturised wells which may adversely effect assay accuracy and precision. This method has the further advantage of reducing the workload required to culture cells for use in assays by use of a large single culture in place of many thousands of individual cultures in microplate wells.

EXAMPLES

The invention is further illustrated by reference to the following examples which present certain preferred embodiments of the invention but are not illustrative of all embodiments.

1. Preparation of Yttrium Oxide (YOx) Loaded CYTODEX ™ Microcarrier Beads i) Preparation of Dextran Solution In a 500 ml beaker with stirring 14 g Dextran TF (MW 200,000) was dissolved in water (33 ml). To this solution was added 50% NaOH (1.8 ml, 2.7 g) and NaBH$_4$ (0.06 g) followed by yttrium oxide (7.5 g).

ii) Preparation of Emulsion Media

A 1000 ml reactor with an anchor-type stirrer was placed into a waterbath at a temperature of 50° C. Emulgator (6 g) was dissolved in ethylene dichloride (100 ml).

iii) Preparation of Dextran-YOx Beads (SEPHADEX ™ Gel Filtration Media)

The dextran solution prepared above was poured into the emulsion media from step ii) with stirring (100 rpm). Dextran beads containing YOx are formed. Epichlorhydrin (2.1 ml) was added and the crosslinking reaction started. The reaction time was 16 hours at 50° C. The beads were washed with acetone, water and ethanol and were dried in an oven at 50° C.

iv) Preparation of CYTODEX™-YOx Microcarriers (DEAE SEPHADEX™ Gel Filtration Media)

In a 100 ml 3-necked reaction vessel was added in order with stirring: 50% NaOH (2.1 ml), water (9.3 ml), NaBH$_4$ (0.05 g), toluene (30 ml) and dried dextran beads (5 g). To this was added a 65% solution of diethylaminoethyl chloride hydrochloride (4.5 ml) and the reaction mixture heated at 60° C. for 4 hours. The beads were neutralised with dilute HCl and washed with 0.9% NaCl. The following batches were prepared by the above method:

CYTODEX™/YOx Microcarriers prepared at 3 g YOx/50 ml dextran;

CYTODEX™/YOx Microcarriers prepared at 5 g YOx/50 ml dextran;

CYTODEX™/YOx Microcarriers prepared at 7.5 g YOx/50 ml dextran.

2. Uptake of Radiolabelled Methionine into CHO Cells Cultured on CYTODEX™/YOx Microcarriers 2.1 Cell Culture Methods CYTODEX™ and CYTODEX™/YOx Microcarrier beads were dispensed into sterile universal containers. Beads were collected by centrifugation at 100 rpm for one minute. Supernatants were removed and replaced with complete Ham's F12 nutrient mix containing 10% (v\v) FCS. Beads were incubated with rolling at 37° C. for 30 minutes. Beads were harvested by centrifugation at 100 rpm for 1 minute. Spent medium was removed and replaced with 10$^7$ cells in 500 µl or less. Beads plus cells were incubated at 37° C. for 20 minutes to permit cell attachment to beads. Fresh Ham's F12 medium was added to a final volume of 4 ml containing 5 mg/ml beads for [$^{35}$S] and 10 mg/ml for [$^{14}$C] or [$^3$H]. Beads were left to roll overnight at 37° C. Following overnight incubation, beads/cells were harvested by centrifugation at 100 rpm for 1 minute. Supernatant containing unattached cells was removed. Microcarrier beads were washed with PBS (×1) and resuspended in methionine deficient DMEM supplemented with radiolabelled methionine. Cultures were returned to 37° C. with rolling. [$^3$H] Methionine and [$^{14}$C] or [$^{35}$S]methionine were included at final concentrations of 8 µCi/ml and 4 µCi/ml respectively.

Following incubation of cells with radiolabelled methionine, 50 µl (250–500 µg beads) aliquots were sampled onto solid white NBS 384 well plates (Corning Costar) and the plate imaged for 5 minutes on a CCD Imaging System (LeadSeeker™, Amersham Pharmacia Biotech).

To demonstrate that uptake of radiolabelled methionine was due to incorporation into cellular proteins and not due to non-specific adsorption of the radiolabel by the beads, experiments were performed in presence and absence of the protein synthesis inhibitor cycloheximide (10 µM final concentration).

2.3 Results

The results are shown in FIGS. 1, 2 and 3 which demonstrate the incorporation of radiolabelled methionines ([$^{35}$S], [$^{14}$C] and [$^3$H]) into CHO cells grown on CYTODEX™/YOx Microcarrier beads. Increases in signal are observed with increasing loading of YOx scintillant. FIG. 1 moreover, illustrates that the uptake of [$^{35}$S]methionine into CHO cells is inhibited in the presence of protein synthesis inhibitor, cycloheximide.

3. Parallel Assays of the Incorporation of [$^{35}$S]methionine into CHO cells and HeLa Cells Cultured on CYTODEX™/YOx Microcarriers 3.1 Preparation of Reagents 40 mg of YOx-loaded CYTODEX™ Microcarrier beads were dispensed into suitable sterile containers and allowed to settle. The supernatant was removed from each microcarrier pellet and the beads resuspended in 5 ml of either complete Ham's F12 nutrient mix (Sigma N-4888) or DMEM (Sigma D-6546), both containing 10% FCS, 2 mM L-glutamine and 50 µg/ml streptamycin/50 IU/ml penicillin. The microcarriers were incubated at 37° C. for thirty minutes without rolling.

10×10$^6$ CHO or HeLa cells in 5 ml complete medium were added to separate microcarrier preparations and the cultures incubated at 37° C. for thirty minutes without rolling. After the initial incubation cultures were incubated overnight at 37° C. with rolling. Following the overnight incubation, unattached cells were removed and the beads resuspended in 10 ml complete culture medium. Microcarriers/cells were maintained in culture until the cell density had reached a sufficient level. Culture medium was replaced every two days.

Cycloheximide was prepared as a 1 mM stock in phosphate buffered saline and added to the cultures at a final concentration of 10 µM.

[$^{35}$S]Methionine (Amersham Pharmacia Biotech—SJ1015) was prepared as an 8 µCi/ml solution in methionine depleted EMEM (Gibco BRL 31900-012) containing 10% FCS, 2 mM L-glutamine and 50 µg/ml streptamycin/50 IU/ml penicillin.

Each microcarrier preparation was allowed to settle and the growth medium removed. Microcarriers were rinsed twice in sterile phosphate buffered saline and resuspended at 10 mg/ml in [$^{35}$S]methionine supplemented medium. Cultures were divided into two and cycloheximide added to a final concentration of 10 µM to one and phosphate buffered saline to the other. The cultures were returned to the incubator with rolling. 50 µl Aliquots of microcarriers were removed at timed intervals onto solid white 384-well microplates. Plates were read on the LEADseeker™ Imaging System with a 5 minute exposure time to detect cellular associated methionine.

3.2 Results

FIG. 4 shows that incorporation of [$^{35}$S]methionine into CHO and HeLa cells can be detected on scintillating microcarriers modified for cell attachment. A signal of 1700 IODs was obtained for CHO cells, 900 IODs for HeLa cells and 650 IODs for 'no cell' controls. In the presence of a protein synthesis inhibitor the signal was reduced to 650 IODs for CHO cells and 600 IODs for HeLa cells.

The use of a microcarrier format overcomes the problem of limited growth surface associated with higher density microplates. For a given plate format, the increased surface area provided by the bead surface permits a greater number of cells per well when compared to growing cells on the base of the well.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A method for the measurement of a cellular process in one or more different populations of cells, the method comprising:
   i) providing one or more different populations of adherent cells growing on support particles, said support particles including a scintillant substance and being adapted for cell growth;
   ii) introducing samples of each of said populations of adherent cells, growing on said support particles, contained in a fluid medium into separate reaction vessels for each population sampled;
   iii) introducing into each reaction vessel a reagent labelled with a radioisotope under conditions so as to cause a portion of said radiolabelled reagent to become associated with said cells; and
   iv) detecting light emission from said support particles, including said scintillant substance caused by radioactive decay of the radioisotope as a means of measuring said cellular process.

2. The method of claim 1 wherein different concentrations of said radiolabelled reagent are incubated in separate reaction vessels in a fluid medium, wherein each fluid medium contains said one or more different populations of cells.

3. The method of claim 1 wherein said vessel is a well of a multiwell plate.

4. The method of claim 1 wherein said detection step is performed in the presence of radiolabelled reagent both associated with said cells and in the fluid medium.

5. The method of claim 1 wherein said detection step is performed by scintillation counting.

6. The method of claim 1 wherein said detection step is performed by imaging.

7. The method of claim 1 wherein said cellular process is selected from biosynthesis, uptake, transport, receptor binding, metabolism, fusion, biochemical response, growth and death.

8. The method of claim 7 wherein said receptor binding comprises a specific binding interaction between the radiolabelled reagent and a specific binding partner located in or on the surface of the cells.

9. The method of claim 1 wherein the radioisotope is selected from $^{14}$C, $^3$H, $^{35}$S, $^{33}$P, $^{125}$I, $^{32}$P, $^{45}$Ca, $^{55}$Fe, $^{51}$Cr, $^{86}$Rb and $^{109}$Cd.

10. The method of claim 1 wherein said measurement of said cellular process is performed in real time using a non-invasive technique.

* * * * *